United States Patent
Renner et al.

(10) Patent No.: US 7,049,471 B2
(45) Date of Patent: May 23, 2006

(54) SEPARATION OF AMINE FROM A PHENOLIC COMPOUND

(75) Inventors: Carl Andrew Renner, Wilmington, DE (US); Richard Frank Dubnansky, Beaumont, TX (US); Freddison A. Parsons, Port Arthur, TX (US); Richard T. Stimek, Beaumont, TX (US); Zhihong Wu, Mobile, AL (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 145 days.

(21) Appl. No.: 10/798,083

(22) Filed: Mar. 11, 2004

(65) Prior Publication Data

US 2005/0080294 A1   Apr. 14, 2005

Related U.S. Application Data

(60) Provisional application No. 60/510,690, filed on Oct. 10, 2003.

(51) Int. Cl.
*C07C 209/86* (2006.01)
(52) U.S. Cl. ...................... 564/437; 564/439
(58) Field of Classification Search ................. 564/437
See application file for complete search history.

(56) References Cited

U.S. PATENT DOCUMENTS 1,942,838 A * 1/1934 Semon ....................... 564/280
3,682,782 A * 8/1972 Choo .......................... 203/91
4,267,390 A   5/1981 Leston
4,267,391 A   5/1981 Leston
4,491,673 A   1/1985 Cutchens et al.
5,192,399 A   3/1993 Sieja

FOREIGN PATENT DOCUMENTS

JP     08 295654 A    12/1996

OTHER PUBLICATIONS

Database CAPLUS on STN, Acc. No. 1933:7185, Bentley et al., FR 732180 (Feb. 23, 1933)(abstract).*
Database CAPLUS on STN, Acc. No. 1932:18384, Suirkin et al., RU 23412 (Oct. 31, 1931)(abstract).*
Database CAPLUS on STN, Acc. No. 1984:138742, Levchenko et al., Su 1051057 (Oct. 30, 1983) (abstract).*
Ventor D L et al., Liquid-liquid equilibria for phenolic compounds, neutral oils, and nitrogen bases at 313.15 K, J. Chem Eng Data; Journal of Chemical and Engineering Data—Jul./Aug. 2001, vol. 46, No. 4, Jul. 2001, pp. 613-622, USA.
Yang, Guo-Hua et al., Simultaneous separation and concentration for phenol and aniline by distillation with added salts. Journal, Dept. of Chemical Engineering Univ. of Petroleum, Dongying, Shandong, 257061, Peop. Rep. China, Ranliao Huaxue Xuebao (2000), 28(4), 364-367.

* cited by examiner

Primary Examiner—Brian Davis

(57) ABSTRACT

A process comprises contacting a product mixture with a base, optionally in the presence of a polyhydric alcohol, to produce a base-treated mixture and distilling the base-treated mixture in which the product mixture comprises an aromatic amine and a phenolic compound.

25 Claims, No Drawings

SEPARATION OF AMINE FROM A PHENOLIC COMPOUND

FIELD OF THE INVENTION

The invention relates to a process for separation of an aromatic amine from a phenolic compound in a mixture comprising the aromatic amine and phenolic compound.

BACKGROUND OF THE INVENTION

Aromatic amines are important industrial chemicals. They can be used to produce a very important class of industrial compounds such as azo dyes. Aromatic amines can be produced by chemical reduction of nitro compounds with a metal and acid such as, for example, iron or tin and hydrochloric acid or by catalytic hydrogenation using molecular hydrogen and a hydrogenation catalyst such as nickel or platinum. Nitro compounds can be readily made by direct nitration of aromatic compounds.

The product mixture produced by catalytic hydrogenation of an aromatic nitro compound generally comprises the desired amine, a corresponding phenolic compound, and unreacted aromatic nitro compound. These by-products, because of their color and deleterious effects on product properties, are undesirable and are difficult to separate from the amines by distillation. Therefore, there is an increasing need for the reduction of impurities to increase the amine purity.

SUMMARY OF THE INVENTION

A process comprises contacting a product mixture with a base, optionally in the presence of a polyhydric alcohol, to produce a base-treated mixture and distilling the base-treated mixture in which the product mixture comprises an aromatic amine and a phenolic compound.

DETAILED DESCRIPTION OF THE INVENTION

An aromatic amine can be produced by catalytic reduction or hydrogenation of an aromatic nitro compound, either under liquid phase or gas phase. The reduction or hydrogenation can be carried out under any suitable conditions known to one skilled in the art, continuously, semi-continuously, or batch-wise. A suitable condition can include a temperature in the range of from about 30° C. to about 300° C., preferably about 80° C. to about 250° C.; a pressure that can accommodate the temperature such as about 1 atm (103 kPa) to about 20 atm (300 psig, 2000 kPa), preferably about 150 kPa to about 800 kPa; and for a sufficient period of time such as from about one to about 100 minutes.

Any hydrogenation catalysts known to one skilled in the art such as, for example, nickel, iron, platinum, copper, cobalt, palladium, iridium, and combinations of two or more thereof can be used in the production of aromatic amine. Generally, a catalyst can be present in a catalytic amount effective to catalyze the hydrogenation or reduction and can be in the range of from about 1 to about 10,000 ppm (mg per kg) aromatic nitro compound.

The hydrogenation or reduction process produces a product mixture or crude product, which comprises desired amine and impurities. A desired amine can have the formula of $RAr(CH_2)_pNR^1$ where Ar is an arylene group; R and each $R^1$ can be the same or different; each $R^1$ is independently selected from the group consisting of hydrogen, halogen, alkyl group, aryl group, and combinations of two or more thereof; and p is a number from 0 to 3. Examples of amine products include, but are not limited to, aniline, toluidines, chloroanilines, bromoanilines, iodoanilines, chlorotoluidines, bromotoluidines, iodotoluidines, benzylamine, N-benzylamine, ethylanilines, fluoromethylanilines, chloromethylanilines, bromomethylanilines, and combinations of two or more thereof. These disclosed examples include all possible isomers.

For example, aniline can be produced by the reduction of nitrobenzene with hydrogen either in the liquid phase using a supported hydrogenation catalyst such as nickel or precious metal, or in the gas phase using supported catalysts. Phenol is a byproduct, in trace amounts ranging from about 50 to about 1000 mg per kg amine product (ppm). Aniline can also be produced by conversion of phenol in the Halcon process.

Also for example, toluidine can be produced by reduction of nitrotoluene. Nitrotoluene can be vaporized at a temperature in the range of from about 150° C. to about 400° C. to obtain a vapor or gas phase of nitrotoluene. The vapor phase nitrotoluene is then introduced or fed to suitable equipment such as a gas phase vessel or reactor, preferably a fixed bed reactor containing a hydrogenation catalyst. Hydrogen can be introduced into the equipment, preferably contemporaneously with the vapor phase nitrotoluene.

Impurities or by-products associated with the production of aromatic anuines include, but are not limited to, unreacted nitro compounds, cyclohexanones, phenolic compounds, ketones, and combinations of two or more thereof. Examples of phenolic compounds include, but are not limited to, phenol, cresols, chlorophenols, bromophenols, iodopheuols, chlorotoluidines, bromotoluidines, iodotoluidines, benzylamine, N-benzylamine, ethylphenols, fluoromethylphenols, chloromethylphenols, bromomethylphenols and combinations of two or more thereof. These disclosed examples include all possible isomers.

Any unreacted nitro compound can be present in the product mixture in the range of from 0 to about 1000 ppm and can be readily removed from the crude product by any means known to one skilled in the art such as, for example, distillation. Because such means are well known, the description of which is omitted herein for the interest of brevity.

Ideally, a desired amine compound contains lower than 500, preferably lower than 100, and more preferably lower than 50 parts per million (mg/kg) of such phenolic compound.

According to the invention, the product mixture (or crude product) can be contacted with a base before it is distilled. Any base, organic or inorganic, can be used. For example, suitable bases can include, without limitation, lithium hydroxide, sodium hydroxide, sodium hydrosulfide, sodium bisulfide, potassium hydroxide, potassium hydrosulfide, potassium bisulfide, calcium hydroxide, magnesium hydroxide, sodium bicarbonate, sodium carbonate, sodium sulfide, sodium oxide, magnesium oxide, calcium oxide, calcium carbonate, sodium phenoxide, barium phenoxide, calcium phenoxide, tetramethylammonium hydroxide, tetraethylammonium hydroxide, tetrapropylammonium hydroxide, tetramethylammonium bisulfide, tetraethylammonium bisulfide, and combinations of any two or more thereof. Potassium hydroxide and sodium hydroxide are preferred for they are readily available and inexpensive.

A base can be combined with the crude product at any concentration effective to reduce the phenolic compound contamination to the desired level disclosed above. Generally, the molar ratio of base to phenolic compound can be in the range of from about 0.5:1 to about 10:1, preferably about 1:1 to about 3:1 or about 1:1 to about 2:1. The contacting of the crude product with a base can be carried out under any suitable conditions. For example, such condition can include a temperature in the range of from about 0° C. to about 200° C., preferably about 20° C. to about 50° C., a pressure that can accommodate the temperature such as about 1 kPa to about 300 kPa, preferably about 10 kPa to about 110 kPa, and for a sufficient period of time such as from about 0.01 to about 10,000 minutes.

Combining a base and an amine can also be carried out in the presence of a polyhydric alcohol. Examples of polyhydric alcohol include, but are not limited to trimethylene glycol, triethylene glycol, glycerols, ethylene glycol, diethylene glycol, 1,2-propane diol, 1,3-propane diol, tripropylene glycol, polyethylene glycols, polypropylene glycols, and combinations of two or more thereof. The polyhydric alcohol can be present in the base-amine combination in the range of from about 1 to about 10,000 mg per kg of the total combination.

Thereafter, a desired amine can be recovered from the base-treated crude product (or product mixture) by, for example, distillation. Suitable apparatus for the distillation is any customary apparatus as described for example in *Kirk-Othmer, Encyclopedia of Chemical Technology*, 3rd Ed. Vol. 7, John Wiley & Sons, New York, 1979, pages 870–881, such as sieve plate columns, bubble cap columns or columns packed with arranged or dumped packing. The distillation can be carried out in a single column or a plurality of columns, such as 2 or more columns. Any distillation techniques known to one skilled in the art can be used. A suitable distillation can include a temperature in the range of from about 100 to about 400, preferably about 100 to about 250° C., a pressure that can accommodate the temperature such as about 0.1 kPa to about 200 kPa, preferably about 5 kPa to about 30 kPa, and for a sufficient period of time such as from about 1 to about 1500 minutes.

EXAMPLES

Example 1

This Example Illustrates Reduction of Phenol in Aniline Using KOH

To a distillation flask was added 100 ml of commercial aniline containing 122 ppm (mg/kg) phenol (a final product produced from a DuPont commercial plant at Beaumont, Tex., USA) and potassium hydroxide (53.5 mg) dissolved in 64.4 mg of water. This was connected to a distillation head containing a short vigreux column. Reduced pressure (42 mmHg (5.6 kPa)) distillation was continued until 75 ml of aniline was in the receiver. GC analysis of the distillate revealed the phenol content was 7.4 ppm. The phenol content of the material still in the distilling flask was 321 ppm based on 25 ml aniline remaining in the flask.

Similarly, 100 ml of commercial aniline and potassium hydroxide (52 mg) in 66 mg of water was added to a distillation flask. This was vacuum distilled at 40 mmHg (5.33 kPa) and three cuts taken, 79.4 g, 8.1 g and 8.4 g. The phenol content of these cuts were respectively 4 ppm, 3 ppm, and <1 ppm (non-detect). The phenol content of the distillation residue was 2391 ppm.

Example 2

This Example Shows Reduction in Phenol Content in Aniline Using NaOH

To a distillation flask was added 100 ml of commercial aniline (phenol 122 ppm) and sodium hydroxide (35.7 mg) dissolved in 93 mg of water. The same procedure as Example 1 was followed. The distillate (75 ml) had a phenol content of 19 ppm. The phenol content of the material remaining in the distilling was 374 ppm.

Example 3

This Example Shows Using KOH and Unrectified Crude Aniline

A series of runs was conducted using a sample of crude, unrectified, aniline obtained from a commercial plant, which had a phenol content of 107 ppm to determine the efficiency of removing phenol with various doses of potassium hydroxide. An unrectified aniline was a crude plant aniline which had been dewatered but not detared in the final (rectifying) distillation column.

To a distillation flask was added 50 ml of crude aniline and 35 µl of 50% potassium hydroxide in water. Distillation was performed at 90 mm Hg (12 kPa) pressure using a five plate Oldershaw column and vacuum distillation head. Distillation was stopped on obtaining 48.9 g of aniline distillate. This had a phenol content of 2.7 ppm. The results are shown in the following table.

| KOH (ppm) | Phenol (ppm) |
|---|---|
| 0 | 107 |
| 216 | 43 |
| 289 | 18 |
| 361 | 17 |
| 433 | 6.8 |
| 433 | 10.4 |
| 505 | 2.7 |
| 578 | 0 |

Example 4

This example Illustrates Using a Polyhydric Alcohol

To a distilling flask was added 50 ml of crude aniline, 40 µl of 50% potassium hydroxide and 100 µl of polyethylene glycol (avg. Mn ca. 400, "PEG 400", Aldrich Chemical Company, Milwaukee, Wis.). The resulting mixture was vacuum distilled at 90 mm giving 46.6 g of aniline distillate containing 1.1 ppm of phenol.

Example 5

This Example Shows Treating o-Toluidine with KOH

Aqueous potassium hydroxide solution (45%; 0.1055 g) was charged into a three neck round bottom flask (500 ml) followed by 123.5 g of o-toluidine (OTOL) containing 489.1 ppm of o-cresol. OTOL was a commercial product commercially available from First Chemical Corp., Pascagoula, Miss. An Aldrich Oldershaw column (ten stages) with a short path distillation head on top of the column was attached to the flask. The mixture in the flask was agitated with a magnetic spin bar while vacuum was gradually pulled down to 90 mmHg (12 kPa). The pot temperature was raised using a heating mantle to distill OTOL. The typical distillation conditions were: pot temperature 130° C., overhead temperature 125° C., vacuum 90 mmHg (12 kPa). The distillation was stopped when boil up slowed down and the overhead temperature started falling. Distillate (108.5 g) was collected and was analyzed with GC to find o-cresol non-detectable.

In separate runs, a plant distilled OTOL sample, obtained from a storage tank, having 133.3 ppm of o-cresol was used. A different amount of o-cresol was added to the sample to make OTOL with different concentrations of o-cresol. The OTOL was then mixed with aqueous KOH solution (45%) at different KOH/o-cresol mole ratios and distilled through a ten-stage Oldershaw column under vacuum. The distillation conditions were similar to the plant OTOL distillation conditions disclosed above. The results summarized in the following table (ND denotes non-detectable) demonstrate that the invention process substantially reduced the o-cresol content in OTOL.

| Run No. | Initial o-Cresol Content (ppm) | KOH/o-Cresol mole ratio | o-Cresol in Distillate (ppm) |
| --- | --- | --- | --- |
| 1 | 489.1 | 1.51/1 | ND |
| 2 | 489.1 | 1.20/1 | ND |
| 3 | 489.1 | 1.08/1 | 31.7 |
| 4 | 489.1 | 0.99/1 | 220.9 |
| 5 | 286.5 | 2.00/1 | ND |
| 6 | 286.5 | 1.60/1 | ND |
| 7 | 286.5 | 0.99/1 | 68 |
| 8 | 133.3 | 1.22/1 | ND |
| 9 | 133.3 | 1.07/1 | 29.6 |
| 10 | 133.3 | 0.99/1 | 38.4 |

Example 6

This Example Shows Using a Polyhydric Alcohol to Stabilize Excess KOH

In another separate run, o-cresol was added to OTOL to raise the o-cresol concentration to 8.8%. About 1.6 equivalent of KOH (45%) was charged. The pot temperature was raised under vacuum to strip water and then to reflux OTOL for 8 hours. At the end of the reflux, OTOL (20% of the charge) was distilled through the ten-stage column. The overhead sample showed 10.1 ppm of o-cresol. The potassium o-cresolate concentration was about 14% in the pot. It was noted that some white salt (excess KOH) coated on the flask bottom. Poly(ethylene glycol) was then added to the pot. The amount of PEG charged was the same as the KOH (45%) charge. After being agitated at 120° C. for 20 minutes, all the salts went into the solution.

What is claimed is:

1. A process comprising contacting a product mixture with a base, optionally in the presence of a polyhydric alcohol, to produce a base-treated mixture, introducing said base-treated mixture to a distillation apparatus, and distilling said base-treated mixture wherein said product mixture comprises an aromatic amine and a phenolic compound.

2. A process according to claim 1 wherein the molar ratio of said base to said phenolic compound is in the range of from about 1:1 to about 4:1.

3. A process according to claim 1 wherein the molar ratio of said base to said phenolic compound is in the range of from about 1:1 to about 2:1.

4. A process according to claim 1 wherein said base is lithium hydroxide, sodium hydroxide, sodium hydrosulfide, sodium bisulfide, potassium hydroxide, potassium hydrosulfide, potassium bisulfide, calcium hydroxide, magnesium hydroxide, sodium bicarbonate, sodium carbonate, sodium sulfide, sodium oxide, magnesium oxide, calcium oxide, calcium carbonate, sodium phenoxide, barium phenoxide, calcium phenoxide, tetramethylammonium hydroxide, tetraethylammonium hydroxide, tetrapropylammonium hydroxide, tetramethylammonium bisulfide, tetraethylammonium bisulfide, or combinations of any two or more thereof.

5. A process according to claim 2 wherein said base is lithium hydroxide, sodium hydroxide, sodium hydrosulfide, sodium bisulfide, potassium hydroxide, potassium hydrosulfide, potassium bisulfide, calcium hydroxide, magnesium hydroxide, sodium bicarbonate, sodium carbonate, sodium sulfide, sodium oxide, magnesium oxide, calcium oxide, calcium carbonate, sodium phenoxide, barium phenoxide, calcium phenoxide, tetramethylammonium hydroxide, tetraethylammonium hydroxide, tetrapropylammonium hydroxide, tetramethylammonium bisulfide, tetraethylammonium bisulfide, or combinations of any two or more thereof.

6. A process according to claim 3 wherein said base is potassium hydroxide, sodium hydroxide, or combinations thereof.

7. A process according to claim 1 wherein said amine is aniline, toluidines, chloroanilines, bromoanilines, iodoanilines, chlorotoluidines, bromotoluidines, iodotoluidines, benzylamine, N-benzylamine, ethylamines, fluoromethylanilines, chloromethylanilines, bromomethylanilines, or combinations of two or more thereof.

8. A process according to claim 5 wherein said amine is aniline, toluidines, chloroanilines, bromoanilines, iodoanilines, chlorotoluidines, bromotoluidines, iodotoluidines, benzylamine, N-benzylamine, ethylanilines, fluoromethylanilines, chloromethylanilines, bromomethylanilines, or combinations of two or more thereof.

9. A process according to claim 6 wherein said amine is aniline, toluidines, or combinations of two or more thereof.

10. A process according to claim 2 wherein said phenolic compound is phenol, cresols, chlorophenols, bromophenols, iodophenols, chlorotoluidines, bromotoluidines, iodotoluidines, benzylamine, N-benzylamine, ethylphenols, fluoromethylphenols, chloromethylphenols, bromomethylphenols, or combinations of two or more thereof.

11. A process according to claim 5 wherein said phenolic compound is phenol, cresols, chlorophenols, bromophenols, iodophenols, chlorotoluidines, bromotoluidines, iodotoluidines, benzylamine, N-benzylamine, ethylphenols, fluoromethylphenols, chloromethylphenols, bromomethylphenols, or combinations of two or more thereof.

12. A process according to claim 8 wherein said phenolic compound is phenol, cresols, chlorophenols, bromophenols, iodophenols, chlorotoluidines, bromotoluidines, iodotoluidines, benzylamine, N-benzylamine, ethylphenols, fluoromethylphenols, chloromethylphenols, bromomethylphenols, or combinations of two or more thereof.

13. A process according to claim 6 wherein said phenolic compound is phenol, cresols, or combinations of two or more thereof.

14. A process according to claim 8 wherein said phenolic compound is phenol, cresols, or combinations of two or more thereof.

15. A process according to claim 14 wherein said contacting is carried out in the presence of a polyhydric alcohol, which is trimethylene glycol, triethylene glycol, glycerol, ethylene glycol, diethylene glycol, 1,2-propane diol, 1,3-propane diol, tripropylene glycol, polyethylene glycol, polypropylene glycol, or combinations of two or more thereof.

16. A process according to claim 15 wherein said polyhydric alcohol is polyethylene glycol.

17. A process comprising contacting a product mixture with a base to produce a base-treated mixture, introducing said base-treated mixture to a distillation apparatus and distilling said base-treated mixture,
wherein said product mixture comprises an aromatic amine and a phenolic compound;
the molar ratio of said base to said phenolic compound is in the range of from about 1:1 to about 4:1;
said base is lithium hydroxide, sodium hydroxide, calcium hydroxide, magnesium hydroxide, sodium bicarbonate, sodium carbonate, sodium oxide, magnesium oxide, calcium oxide, calcium carbonate, tetramethylammonium hydroxide, tetraethylammonium hydroxide, tetrapropylammonium hydroxide, tetramethylammonium bisulfide, tetraethylammonium bisulfide, or combinations of any two or more thereof; and
said amine is aniline, toluidines, chloroanilines, bromoanilines, iodoanilines, chlorotoluidines, bromotoluidines, iodotoluidines, benzylamine, N-benzylamine, ethylanilines, fluoromethylanilines, chloromethylanilines, bromomethylanilines, or combinations of two or more thereof.

18. A process according to claim 17 wherein said contacting is carried out in the presence of a polyhydric alcohol.

19. A process according to claim 17 wherein the molar ratio of said base to said phenolic compound is in the range of from about 1:1 to about 2:1; said amine is aniline, toluidines, or combinations of two or more thereof; said phenolic compound is phenol, cresols, or combinations of two or more thereof and said base is potassium hydroxide, sodium hydroxide, or combinations thereof.

20. A process according to claim 19 wherein said contacting is carried out in the presence of a polyhydric alcohol, which is trimethylene glycol, triethylene glycol, glycerol, ethylene glycol, diethylene glycol, 1,2-propane diol, 1,3-propane diol, tripropylene glycol, polyethylene glycol, polypropylene glycol, or combinations of two or more thereof.

21. A process according to claim 20 wherein said polyhydric alcohol is polyethylene glycol.

22. A process for separating o-cresol from o-toluidine in a mixture, which comprises said o-cresol and said o-toluidine, comprising contacting said mixture with potassium hydroxide to produce a base-treated mixture and distilling said base-treated mixture.

23. A process according to claim 22 wherein said process is carried out in the presence of a polyhydric alcohol.

24. A process according to claim 23 wherein said polyhydric alcohol is polyethylene glycol.

25. A process according to claim 1 wherein said contacting is carried out in the presence of a polyhydric alcohol.

* * * * *